United States Patent [19]
Krstenansky et al.

[11] Patent Number: 5,574,012
[45] Date of Patent: Nov. 12, 1996

[54] ANALOGS OF HIRUDIN HAVING ANTI-PLATELET ACTIVITY

[75] Inventors: John L. Krstenansky, Palo Alto, Calif.; Robert J. Broersma, Jr., Noblesville, Ind.

[73] Assignee: Merrell Pharmaceuticals Inc., Cincinnati, Ohio

[21] Appl. No.: 444,618

[22] Filed: May 19, 1995

Related U.S. Application Data

[63] Continuation of Ser. No. 255,846, Jun. 8, 1994, abandoned, which is a continuation of Ser. No. 714,547, Jun. 11, 1991, abandoned, which is a continuation-in-part of Ser. No. 557,289, Jul. 24, 1990, abandoned.

[51] Int. Cl.$^6$ .............................. A61K 38/00; C07K 5/00; C07K 7/00
[52] U.S. Cl. ............................... 514/14; 514/15; 514/12; 530/327; 530/324
[58] Field of Search .................................... 514/12, 13, 14, 514/15; 530/324, 330, 327

[56] References Cited

U.S. PATENT DOCUMENTS

| | | | |
|---|---|---|---|
| 4,668,662 | 5/1987 | Tripier | 514/12 |
| 4,767,742 | 8/1988 | Dodt et al. | 514/12 |
| 4,792,525 | 12/1988 | Ruoslahti et al. | 435/240.243 |
| 4,971,953 | 11/1990 | Krstenansky | 514/14 |
| 5,192,745 | 3/1993 | Krstenansky et al. | 514/15 |
| 5,192,747 | 3/1993 | Krstenansky | 514/15 |
| 5,232,912 | 8/1993 | Krstenansky et al. | 514/15 |
| 5,236,898 | 8/1993 | Krstenansky et al. | 514/9 |
| 5,279,812 | 1/1994 | Krstenansky et al. | 424/1.1 |

FOREIGN PATENT DOCUMENTS

| | | |
|---|---|---|
| 0276014 | 7/1988 | European Pat. Off. . |
| 0332523 | 9/1989 | European Pat. Off. . |
| 0333356 | 9/1989 | European Pat. Off. . |
| 0341607 | 11/1989 | European Pat. Off. . |
| 0421367 | 2/1991 | European Pat. Off. . |
| 0372503 | 2/1991 | European Pat. Off. . |
| 0421366 | 4/1991 | European Pat. Off. . |

OTHER PUBLICATIONS

Pierschbacker et al., J. of Biol Chem., vol. 262, No. 26, pp. 17294–17298, 1987.
Lam et al., J. of Biol. Chem., vol. 262, No. 3, pp. 947–950, 1987.
Maraganore et al, J. of Biol Chem., vol. 264, No. 15, pp. 8692–8698, 1989.
The Merck Manual, Thirteenth Edition (1977), pp. 302–308.
The Merck Manual, Thirteenth Edition (1977), pp. 606–608.
The Merck Manual, Thirteenth Edition (1977), pp. 1926–1927.
Hoffmann A. et al., "Inhibition of the Thrombin–Platelet Reaction by Hirudin" Haemostasis 14:164–169 (1984).
Markwardt F. et al., "Comparative Studies on Thrombin Inhibitors in Experimental Microthrombosis". Thrombosis and Haemostasis (Stuttgart 49 (3) 235–237 (1983).
Church et al., "Chimeric Antithrombin Peptide," J. Biol. Chem., vol. 266, No. 18, pp. 11975–11979 (1991).
Krstenansky, et al., "Development of MDL 28,050, a Small Stable Antithrombin Agent Based on a Functional Domain of the Leech Protein, Hirudin," Thromb. Haem. vol. 63 (2):208–214 (1990).
Krstenansky, et al., "C–Terminal Peptide Alcohol, Acid and Amide Analogs of Desulfato Hirudin 54–65 as Antithrombin Agents," Thromb. Research 54:319–325 (1989).
Krstenansky, et al., "Anticoagulant Peptides: Nature of the Interaction of the C–Terminal Region of Hirudin with a Noncatalytic Binding Site on Thrombin," J. Med. Chem. 30:1688–1691 (1987).
Chemical Abstract 109:231560t p. 918 (1988) abstracting Krstenansky, et al., "Preparation of hirudin segments as anticoagulants," EP Appl 276,014.
Krstenansky, et al., "Comparison of Hirudin and Hirudin PA C–Terminal Fragments and Related Analogs as Antithrombin Agents," Thromb. Research, vol. 52(2):137–141 (1988).
Krstenansky, et al., "Antithrombin Properties of C–terminus of Hirudin using Synthetic unsulfated N–acetyl–hirudin 45–65," FEBS Lett. 211(1) 10–16 (1987).
Bajusz, et al., "Thrombin Inhibition by Hirudin Fragments: Possible Mechanism of Hirudin–Thromein Interaction," Peptides 32:473–476 (1984).
Dodt, et al., "The complete amino acid sequence of hirudin, a thrombin specific inhibitor," FEBS Letters 165(2), 180–84 (1984).
Owen, et al., "N–Terminal Requirements of Small Peptide Anticoagulants Based on Hirudin 54–65," J. Med. Chem., 31, 1009–1011 (1988).
Krstenansky, et al., "Characterization of the Interaction of Thrombin with the Carboxyl–terminal Region of the Leech Anticoagulant Peptide Hirudin," *Peptides: Chemistry and Biology*, 1987, pp. 447–448.
Minar, et al., abstract of "Local Hirudin Application," Klin Wochenschr 63(4): 190–1 (1985).

*Primary Examiner*—Avis M. Davenport
*Attorney, Agent, or Firm*—William R. Boudreaux

[57] ABSTRACT

This invention relates to peptide derivatives which are useful anticoagulant agents.

22 Claims, No Drawings

ANALOGS OF HIRUDIN HAVING ANTI-PLATELET ACTIVITY

CROSS-REFERENCE TO RELATED APPLICATION

This is a continuation of application Ser. No. 08/255,846, filed Jun. 8, 1994, now abandoned, which is a continuation of Ser. No. 07/714,547 filed Jun. 11, 1991 now abandoned which is a continuation in part of Ser. No. 07/557,289 filed Jul. 24, 1990 now abandoned which is herein incorporated by reference.

FIELD OF THE INVENTION

This invention relates to peptide analogs having medical use as as anticoagulant and antiplatelet agents.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Antiplatelet agents are useful therapeutic agents in the pharmacological treatment of those platelet associated thromboembolic diseases that are primarily arterial in origin. For example, antiplatelet agents can be used to prevent reoccurence myocardial infarction and strokes.

Hirudin is a 65 residue polypeptide isolated from the salivary glands of leeches. It is an anticoagulant agent, which is a thrombin specific inhibitor. Although quite potent, clinical use of hirudin isolated from leech extracts seems unlikely because of its limited quantity, expense and allergic reactions which commonly follow administration of any foreign protein of this size.

Applicant has previously discovered a specific region of hirudin that is responsible, at least in part, for its anticoagulant activity. This region has been chemically synthesized and certain of its analogs appear to bind to the recognition site of thrombin but not the enzymatic cleavage site which is spatially separate. Binding of the synthetic peptides competitively prevents binding of the fibrinogen to the recognition site of thrombin, a prerequisite to fibrin production and clot formation.

Several reports have described the ability of the oligopeptide Arg-Gly-Asp and related peptides to inhibit the platelet-dependent thrombus formation. Y. Cadroy, et al., *J. Clin. Invest.* 84, 939–944 (1989). Applicant has discovered several means of incorporating both the antiplatelet Arg-Gly-Asp fragment and the previously noted Hirudin C-terminal fragment antithrombin analogs into a single entity having both actions.

SUMMARY OF THE INVENTION

Peptide derivatives of the formula

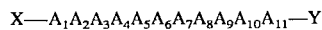  (1)

wherein

X is an amino terminal residue selected from aminomethylbenzoyl, guanidinomethylbenzoyl, guanidinomethylcyclohexylcarbonyl, aminomethylcyclohexylcaronyl, hydrogen, alkyl substituted guanidino or alkyl substituted amino;

$A_1$ is Gly or a bond;
$A_2$ is Asp;
$A_3$ is Phe, SubPhe, β-(2- and 3-thienyl)alanine, β-(2-and 3-furanyl)alanine, β-(2-, 3-, and 4-pyridyl)alanine, β-(benzothienyl-2- and 3-yl)alanine, β-(1- and 2-naphthyl)alanine, Tyr or Trp;
$A_4$ is Glu, Asp, Ser($OSO_3H$), Ser($OPO_3H$), hSer($OSO_3H$), cysteic acid or homocysteic acid;
$A_5$ is any amino acid;
$A_6$ is Ile, Val, Leu, Nle, or Phe;
$A_7$ is Pro, Hyp, 3,4-dehydroPro, thiazolidine-4-carboxylate, Sar, NMePgl or D-Ala;
$A_8$ is any amino acid;
$A_9$ is any amino acid;
$A_{10}$ is a lipophilic amino acid selected from Tyr, Trp, Phe, Leu, Nle, Ile, Val, Cha and Pro or is a dipeptide containing at least one of these lipophilic amino acids;
$A_{11}$ is a bond or is a peptide fragment containing from one to five residues of any amino acid; and
Y is a carboxy terminal residue selected from OH, $C_1$–$C_6$ alkoxy, amino, mono- or di-($C_1$–$C_4$) alkyl substituted amino, or benzylamino;

and the pharmaceutically acceptable salts thereof are useful anticoagulant agents.

DETAILED DESCRIPTION OF THE INVENTION

The following common abbreviations of the amino acids are used throughout this specification:

Gly—glycine
Ala—alanine
Val—valine
Leu—leucine
Ile—isoleucine
Cha—cyclohexylalanine
Orn—ornithine
Pro—proline
Phe—phenylalanine
Trp—tryptophan
Met—methionine
Ser—serine
Thr—threonine
Cys—cysteine
Tyr—tyrosine
Asn—asparagine
Gln—glutamine
Asp—aspartic acid
Glu—glutamic acid
Lys—lysine
Hly—homolysine
Arg—arginine
Har—homoarginine
His—histidine
Nle—norleucine
Hyp—hydroxyproline
Glt—glutaryl
Mal—maleyl
Npa—β-(2-naphthyl)alanine
3,4-dehydroPro—3,4-dehydroproline
Tyr($SO_3H$)—tyrosine sulfate Pgl—phenylglycine
NMePgl—N-methyl-phenylglycine
Sar—sarcocine (N-methylglycine)
pSubPhe—para substituted phenylalanine
SubPhe—ortho, meta, or para, mono- or di- substituted phenylalanine
DAla—D-alanine
Ac—acetyl
Suc—succinyl
pClPhe—para-chloro-phenylalanine
pNO$_2$Phe—para-nitro-phenylalanine
Tyr(Me)—O'-methyl-4-tyrosine
5GP—5-guanidinopentyl
5AP—5-aminopentyl An alkyl group and the alkyl portion of an alkoxy group is taken to include straight, branched, or cyclic alkyl groups, for example, methyl, ethyl, propyl, isopro- pyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. A halogen group is a fluoro, chloro, bromo or iodo group.

The term "any amino acid" as used herein includes the naturally occurring amino acids as well as other "nonprotein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, Ser(OSO$_3$H), hSer(OSO$_3$H), cysteic acid, homocysteic acid, cyclohexylglycine (Chg), α-amino-n-butyric acid (Aba), cyclohexylalanine (Cha), aminophenylbutyric acid (Pba), phenylalanines substituted at the ortho, meta, or paraposition of the phenyl moiety with one or two of the following, a (C$_1$–C$_4$) alkyl, (C$_1$–C$_4$) alkoxy, halogen, or nitro groups or substituted with a methylenedioxy group, β-2- and 3-thienylalanine, β-2- and 3-furanylalanine, β-2-, 3-, and 4-pyridylalanine, β-(benzothienyl-2- and 3-yl)alanine, β-(1- and 2-naphthyl)alanine, O-alkylated derivates of serine, threonine, or tyrosine, S-alkylated cysteine, the O-sulfate ester of tyrosine, 3,5-diiodotyrosine and the D-isomers of the naturally occurring amino acids. The term "any amino acid" is also intended to encompass those naturally occurring and non-protein α-amino acids of the formulae

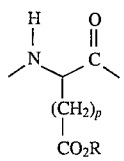

2

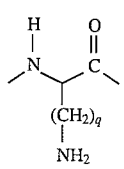

3 and

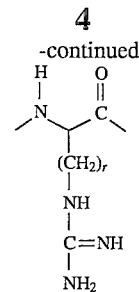

4 wherein p, q, and r are each independently an integer of from 1 to 5 and wherein R is a hydrogen or a (C$_1$–C$_4$)alkyl group.

The term "lipophilic amino acid" includes Tyr, Phe, Leu, Nle, Ile, Val, His and Pro.

The natural amino acids with the exception of glycine, contain a chiral carbon atom. Unless otherwise specifically indicated, the optically active amino acids, referred to herein, are of the L-configuration, including those amino acids depicted by formulae 2, 3, and 4. For example, any of the amino acids of the A$_1$ or A$_{10}$ group can be of the D- or L-configuration. As is customary, the structure of peptides written out herein is such that the amino terminal end is on the left side of the chain and the carboxy terminal end is on the right side of the chain. As is also customary when using the three-letter code for the amino acids, a three-letter code beginning with an upper case letter indicates the L-configuration and a three-letter code beginning with a lower-case letter indicates the D-configuration.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

As with any generic group of chemical compounds, certain groups are preferred. Applicants prefer those peptide derivatives of formula 1 wherein X is aminomethylbenzoyl, guanidinomethylbenzoyl, guanidinomethylcyclohexylcarbonyl, aminomethylcyclohexylcarbonyl, or alkyl substituted amino.

Also preferred are those formula 1 compounds wherein
A$_1$ is Gly or a bond;
A$_2$ is Asp;
A$_3$ is Phe, Trp, or Tyr(OCH$_3$);
A$_4$ is Glu, or Asp;
A$_5$ is Pro;
A$_6$ is Ile or Leu;
A$_7$ is Pro;
A$_8$ is Glu or Asp;
A$_9$ is Glu or Phe;

$A_{10}$ is Ala-Cha, Trp or Phe;
$A_{11}$ is Glu or glu; and
Y is OH or $NH_2$.

Especially preferred are those peptide derivatives of formula 1 wherein

X is an amino terminal residue selected from aminomethylbenzoyl, guanidinomethylbenzoyl, guanidinomethylcyclohexylcarbonyl, aminomethylcyclohexylcaronyl, hydrogen, alkyl substituted guanidino or alkyl substituted amino;

$A_1$ is Gly or a bond;
$A_2$ is Asp;
$A_3$ is Phe, Trp, or Tyr($OCH_3$);
$A_4$ is Glu;
$A_5$ is Pro;
$A_6$ is Ile;
$A_7$ is Pro;
$A_8$ is Glu;
$A_9$ is Glu;
$A_{10}$ is Ala-Cha;
$A_{11}$ is glu; and
Y is OH.

The proteins of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide sythesizer. In this procedure an α-amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky, et al., *Chem. Ind.* (*London*) 38, 1597–98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta*, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl)-l-methylethoxycarbonyl, α,α-dimethyl-3, 5dimethoxybenzyloxycarbonyl and benzhydryloxycarbonyl; (3) aliphatic urethan protecting groups such as tertbutyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(y-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups can be removed by procedures well known in the art. Typically protecting group removal is done after the peptide chain synthesis is complete but the protecting groups can be removed at any other appropriate time.

The antiplatelet dose of a peptide analog of this invention is from 0.2 mg/kg to 250 mg/kg of patient body weight per day depending on the patient, the severity of the thrombotic condition to be treated and the peptide analog selected. The suitable dose for a particular patient can be readily determined. Preferably from 1 to 4 daily doses would be administered typically with from 5 mg to 100 mg of active compound per dose.

Antiplatelet therapy is indicated for the prevention of recurrence of myocardial infarction and stroke as well as other disease conditions associated with platelet aggregation. Those experienced in this field are readily aware of the circumstances requiring anticoagulant and antiplatelet therapy. The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can contain a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Preparation of 5GP-Gly-Asp-Trp-Glu-Pro-Ile-Pro-Glu-Glu-Ala-Cha-glu-OH

The peptide was synthesized by solid-phase methods using 0.1 mmol of a 0.66 mmol/g Boc-(Bzl)D-Glu- resin. Double symmetrical anhydride couplings were performed with 2.0 mmol Nα-Boc-amino acid (Peptides International). The side chain protection utilized was: Asp(Chx), Trp(CHO), Glu(Bzl). Upon completion of the synthesis the Nα-Boc protection was removed with 50% trifluoroacetic acid in methylene chloride. The resin was washed three times with methylene chloride, neutralized with three washings of 10% diisopropylethylamine in methylene chloride, washed three times with methylene chloride, and dried in vacuo. The peptide was deprotected and cleaved from the resin with HF containing 2% anisole at 0° C., for 35 min. The HF was removed in vacuo at 0° C., the peptide precipitated with ethyl ether, extracted from the resin with 30% aqueous acetic acid and lyophilized.

Half of this crude 5-AP analog was treated with O-methylisourea at 5° C. for 16 hours to yield the crude 5-GP analog.

The peptide was purified by desalting on a 92×2.6 cm Sephadex G-15 column in 5% aqueous acetic acid and lyophilized. Preparative HPLC was performed on a $C^{18}$ Vydac 218TP1010 (250×10 mm) column with 24% acetonitrile in 0.1% aqueous trifluoroacetic acid at 5 ml/min. The major peak was collected and lyophilized. Homogeneity was determined by HPLC and TLC.

In the same manner, the peptides of the following example 2–6 were prepared.

EXAMPLE 2

5AP-Gly-Asp-Trp-Glu-Glu-Ile-Pro-Glu-Glu-Ala-Cha-glu-OH

EXAMPLE 3

Arg-Gly-Asp-Trp-Glu-Pro-Ile-Pro-Glu-Glu-Ala-Cha-glu-OH

EXAMPLE 4

5AP-Gly-Asp-Tyr($OCH_3$)-Glu-Pro-Ile-Pro-Glu-Glu-Ala-Cha-glu-OH

EXAMPLE 5

Suc-Tyr-Glu-Pro-Ile-Pro-Arg-Gly-Asp-Phe-glu-OH

EXAMPLE 6

5GP-Gly-Asp-Tyr(OCH3)-Glu-Pro-Ile-Pro-Glu-Glu-Ala-Cha-glu-OH

EXAMPLE 7

4-Aminomethylbenzoyl-Asp-Trp-Glu-Pro-Ile-Pro-Glu-Glu-Ala-Cha-glu-OH

EXAMPLE 8

4-Guanidinomethylbenzoyl-Asp-Trp-Glu-Pro-Ile-Pro-Glu-Glu-Ala-Cha-glu-OH

EXAMPLE 9

4-Aminomethyl-Asp-Trp-Glu-Pro-Ile-Pro-Glu-Glu-Ala-Cha-glu-OH

EXAMPLE 10

4-Guanidinomethylcyclohexylcarbonyl-Asp-Trp-Glu-pro-Ile-Pro-Glu-Glu-Ala-Cha-glu-OH

EXAMPLE 11

4-Aminomethylcyclohexylcarbonyl-Gly-Asp-Phe-Glu-pro-Ile-Pro-Glu-Glu-Ala-Cha-glu-OH

EXAMPLE 12

4-Guanidinomethylcyclohexylcarbonyl-Gly-Asp-Phe-Glu-Pro-Ile-Pro-Glu-Glu-Ala-Cha-glu-OH The peptides of examples 1–2 have the following properties:

| EXAMPLE No. | Amino Acids Analysis (6N HCl Hydrolysis; 24 Hrs at 105° C.) |      |      |      |      |      |      |
|---|---|---|---|---|---|---|---|
|   | B | Z | Arg | Pro | Ala | Gly | Ile |
| 1 | 0.64 | 4.06 | 1.07 | 2.01 | 1.01 | 0.96 | 0.96 |
| 2 | 0.60 | 4.07 | 1.08 | 1.85 | 1.08 | 0.99 | 0.84 |
| 3 | 0.66 | 4.08 | 1.02 | 1.97 | 1.02 | 0.99 | 0.96 |
| 4 | 0.98 | 4.09 | 1.04 | 1.95 | 1.04 | 0.98 | 0.96 |
| 5 | 1.02 | 4.09 | 0.97 | 1.97 | 0.97 | 0.98 | 1.01 |
| 6 | 0.99 | 1.96 | 1.02 | 1.98 | 1.02 | 0.99 | 0.97 |

| Physical Characteristics | |
|---|---|
| EXAMPLE NO. | FAB-MS (M + H) |
| 1 | 1564.5 |
| 2 | 1523.3 |
| 3 | 1580.0 |
| 4 | 1514.1 |
| 5 | 1322.9 |
| 6 | 1556.4 |

| EXAMPLE NO. | Bovine Antithrombin $IC_{50}$ (μM) | Dog Antiplatelet $IC_{50}$ (μM) |
|---|---|---|
| 1 | 1.6 | 6 |
| 2 | 1.7 | 250 |
| 3 | 2.8 | 7 |
| 4 | 5.4 | 280 |
| 5 | 15 | 42 |
| 6 | 5.9 | 10 |
| 7 | 2.1 |  |
| 8 | 1.3 |  |
| 9 | 3.5 |  |
| 10 | 2.3 |  |

What is claimed is:

1. A method of reducing platelet aggregation in a patient in need thereof which comprises administering to the patient an antiplatelet effective amount of a pepside analog of the formula $$X—A_1A_2A_3A_4A_5A_6A_7A_8A_9A_{10}A_{11}—Y$$

wherein

X is an amino terminal residue selected from aminomethylbenzoyl, guanidinomethylbenzoyl, guanidinomethylchyclohexylcarbonyl, aminomethylcyclohexylcarbonyl, alkyl substituted guanidino or alkyl substituted amino;

$A_1$ is Gly or a bond;

$A_2$ is ASP;

$A_3$ is Phe, Trp or Tyr(OCH$_3$);

$A_4$ is Glu;

$A_5$ is Pro or Glu;

$A_6$ is Ile;

$A_7$ is Pro;

$A_8$ is Glu;

$A_9$ is Glu;

$A_{10}$ is Ala-Cha;

$A_{11}$ is glu; and

Y is a carboxy terminal residue selected from OH, $C_1$–$C_6$ alkoxy, amino, mono- or di-($C_1$–$C_4$)alkyl substituted amino or benzylamino;

or a pharmaceutically acceptable salt thereof.

2. A method of claim 1 wherein the peptide analog is 5GP-Gly-Asp-Trp-Glu-Pro-Ile-Pro-Glu-Glu-Ala-Cha-glu-OH (SEQ ID No. 5).

3. A method of claim 1 wherein the peptide analog is 5AP-Gly-Asp-Trp-Glu-Glu-Ile-Pro-Glu-Glu-Ala-Cha-glu-OH (SEQ ID No. 6).

4. A method of claim 1 wherein the peptide analog is 5AP-Gly-Asp-Tyr(Me)-Glu-Pro-Ile-Pro-Glu-Glu-Ala-Cha-glu-OH (SEQ ID No. 8).

5. A method of claim 1 wherein the peptide analog is 5GP-Gly-Asp-Tyr(Me)-Glu-Pro-Ile-Pro-Glu-Glu-Ala-Cha-glu-OH (SEQ ID No. 10).

6. A method of claim 1 wherein the peptide analog is 4-Aminomethylbenzoyl-Asp-Trp-Glu-Pro-Ile-Pro-Glu-Glu-Ala-Cha-glu-OH (SEQ ID No. 11).

7. A method of claim 1 wherein the peptide analog is 4-Guanidinomethylbenzoyl-Asp-Trp-Glu-Pro-Ile-Pro-Glu-Glu-Ala-Cha-glu-OH (SEQ ID No. 12).

8. A method of claim 1 wherein the peptide analog is 4-Aminomethyl-Asp-Trp-Glu-Pro-Ile-Pro-Glu-Glu-Ala-Cha-glu-OH (SEQ ID No. 13).

9. A method of claim 1 wherein the peptide analog is 4-Guanidinomethylcyclohexylcarbonyl-Asp-Trp-Glu-Pro-Ile-Pro-Glu-Glu-Ala-Cha-glu-OH (SEQ ID No. 14).

10. A method of claim 1 wherein the peptide analog is 4-Aminomethylcyclohexylcarbonyl-Gly-Asp-Phe-Glu-Pro-Ile-Pro-Glu-Glu-Ala-Cha-glu-OH (SEQ ID No. 15).

11. A method of claim 1 wherein the peptide analog is 4-Guanidinomethylcyclohexylcarbonyl-Gly-Asp-Phe-Pro-Ile-Pro-Glu-Glu-Ala-Cha-glu-OH (SEQ ID No. 16).

12. A method of reducing blood coagulation in a patient in need thereof which comprises administering to the patient an anticoagulant effective amount of a peptide analog of the formula $$X—A_1A_2A_3A_4A_5A_6A_7A_8A_9A_{10}A_{11}—Y$$

wherein

X is an amino terminal residue selected from aminomethylbenzoyl, guanidinomethylbenzoyl, guanidinomethylchyclohexylcarbonyl, aminomethylcyclohexylcarbonyl, alkyl substituted guanidino or alkyl substituted amino;

$A_1$ is Gly or a bond;

$A_2$ is Asp;

$A_3$ is Phe, Trp or Tyr(OCH$_3$);

$A_4$ is Glu;

$A_5$ is Pro or Glu;

$A_6$ is Ile;

$A_7$ is Pro;

$A_8$ is Glu;

$A_9$ is Glu;

$A_{10}$ is Ala-Cha;

$A_{11}$ is glu; and

Y is a carboxy terminal residue selected from OH, $C_1$–$C_6$ alkoxy, amino, mono- or di-($C_1$–$C_4$)alkyl substituted amino or benzylamino;

or a pharmaceutically acceptable salt thereof.

13. A method of claim 12 wherein the peptide analog is 5GP-Gly-Asp-Trp-Glu-Pro-Ile-Pro-Glu-Glu-Ala-Cha-glu-OH (SEQ ID No. 5).

14. A method of claim 12 wherein the peptide analog is 5AP-Gly-Asp-Trp-Glu-Glu-Ile-Pro-Glu-Glu-Ala-Cha-glu-OH (SEQ ID No. 6).

15. A method of claim 12 wherein the peptide analog is 5AP-Gly-Asp-Tyr(Me)-Glu-Pro-Ile-Pro-Glu-Glu-Ala-Cha-glu-OH (SEQ ID No. 8).

16. A method of claim 12 wherein the peptide analog is 5GP-Gly-Asp-Tyr(Me)-Glu-Pro-Ile-Pro-Glu-Glu-Ala-Cha-glu-OH (SEQ ID No. 10).

17. A method of claim 12 wherein the peptide analog is 4-Aminomethylbenzoyl-Asp-Trp-Glu-Pro-Ile-Pro-Glu-Glu-Ala-Cha-glu-OH (SEQ ID No. 11).

18. A method of claim 12 wherein the peptide analog is 4-Guanidinomethylbenzoyl-Asp-Trp-Glu-Pro-Ile-Pro-Glu-Glu-Ala-Cha-glu-OH (SEQ ID No. 12).

19. A method of claim 12 wherein the peptide analog is 4-Aminomethyl-Asp-Trp-Glu-Pro-Ile-Pro-Glu-Glu-Ala-Cha-glu-OH (SEQ ID No. 13).

20. A method of claim 12 wherein the peptide analog is 4-Guanidinomethylcyclohexylcarbonyl-Asp-Trp-Glu-pro-Ile-Pro-Glu-Glu-Ala-Cha-glu-OH (SEQ ID No. 14).

21. A method of claim 12 wherein the peptide analog is 4-Aminomethylcyclohexylcarbonyl-Gly-Asp-Phe-Glu-pro-Ile-Pro-Glu-Glu-Ala-Cha-glu-OH (SEQ ID No. 15).

22. A method of claim 12 wherein the peptide analog is 4-Guanidinomethylcyclohexyicarbonyl-Gly-Asp-Phe-Glu-pro-Ile-Pro-Glu-Glu-Ala-Cha-glu-OH (SEQ ID No. 16).

* * * * *

UNITED STATES PATENT AND TRADEMARK OFFICE
CERTIFICATE OF CORRECTION

PATENT NO. : 5,574,012

DATED : November 12, 1996

INVENTOR(s) : John L. Krstenansky and Robert J. Broersma, Jr.

It is certified that error appears in the above-identified patent and that said Letters Patent is hereby corrected as shown below:

At column 2, line 4, and again at column 5, line 9, the patent reads "aminomethylcyclohexylcaronyl" and should read --aminomethylcyclohexylcarbonyl--.
At column 6, line 12, the patent reads "3,5dimethoxybenzyloxycarbonyl" and should read --3,5-dimethoxybenzyloxycarbonyl--.
At column 8, line 13, --(SEQ ID No. 5)-- should appear after the title of Example 1.
At column 8, line 46, --(SEQ ID No.6)-- should appear after the title of Example 2.
At column 8, line 50, --(SEQ ID No. 7)-- should appear after the title of Example 3.
At column 8, line 55, --(SEQ ID No. 8)-- should appear after the title of Example 4.
At column 8, line 58, --(SEQ ID No. 9)-- should appear after the title of Example 5.
At column 8, line 62, --(SEQ ID No. 10)-- should appear after the title of Example 6.
At column 8, line 67, --(SEQ ID No. 11)-- should appear after the title of Example 7.
At column 9, line 4, --(SEQ ID No. 12)-- should appear after the title of Example 8.
At column 9, line 8, --(SEQ ID No. 13)-- should appear after the title of Example 9.
At column 9, line 13, --(SEQ ID No. 14)-- should appear after the title of Example 10.
At column 9, line 11 and again at line 16, the term "pro" should read --Pro--.
At column 9, line 17, --(SEQ ID No. 15)-- should appear after the title of Example 11.
At column 9, line 21, --SEQ ID No. 16)-- should appear after the title of Example 12.
At column 21, line 35, in claim 1, the patent reads "amount of a pepside" and should read -- amount of a peptide--.
At column 24, line 20, claim 21 and again at column 24, line 24, claim 22, the term "pro" should read --Pro--.

Signed and Sealed this

Twenty-eighth Day of July, 1998

Attest:

BRUCE LEHMAN

*Attesting Officer*          *Commissioner of Patents and Trademarks*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
 ( A ) LENGTH: 11 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:1:

Thr Pro Lys Pro Gln Ser His Asn Asp Gly Asp
1               5                   10

( 2 ) INFORMATION FOR SEQ ID NO:2:

( i ) SEQUENCE CHARACTERISTICS:
 ( A ) LENGTH: 12 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:2:

Ser Thr Pro Asn Pro Glu Ser His Asn Asn Gly Asp
1               5                   10

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
His  Asn  Asp  Gly  Asp
1                    5
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Asn  Asp  Gly  Asp
1
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Gly at location 1 is
            substituted on the alpha carbon by a 5-guanadino
            pentyl group"

( i x ) FEATURE:
        ( A ) NAME/KEY: Modified-site
        ( B ) LOCATION: 11
        ( D ) OTHER INFORMATION: /note="Xaa at location 11 is a
            cyclohexylalanine"

( i x ) FEATURE:
        ( A ) NAME/KEY: Modified-site
        ( B ) LOCATION: 12
        ( D ) OTHER INFORMATION: /note="Glu at location 12 is
            D- configuration"

( x i ) SEQUENCE DESCRIPTION: SEQ ID NO:5:

```
Gly  Asp  Trp  Glu  Pro  Ile  Pro  Glu  Glu  Ala  Xaa  Glu
1                   5                        10
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Gly at location 1 is
            substituted on the alpha carbon by a 5-amino
            pentyl group"

( i x ) FEATURE:
    ( A ) NAME/KEY: Modified-site
    ( B ) LOCATION: 11
    ( D ) OTHER INFORMATION: /note="Xaa at location 11 is a
        cyclohexylalanine"

( i x ) FEATURE:
    ( A ) NAME/KEY: Modified-site
    ( B ) LOCATION: 12
    ( D ) OTHER INFORMATION: /note="Glu at location 12 is
        D- configuration"

( x i ) SEQUENCE DESCRIPTION: SEQ ID NO:6:

Gly Asp Trp Glu Glu Ile Pro Glu Glu Ala Xaa Glu
1               5                          10

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /note="Xaa at location 12 is a
            cyclohexylalanine"

( i x ) FEATURE:
        ( A ) NAME/KEY: Modified-site
        ( B ) LOCATION: 13
        ( D ) OTHER INFORMATION: /note="Glu at location 13 is
            D- configuration"

( x i ) SEQUENCE DESCRIPTION: SEQ ID NO:7:

Arg Gly Asp Trp Glu Pro Ile Pro Glu Glu Ala Xaa Glu
1                   5                        10

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Gly at location 1 is
            substituted on the alpha carbon by a 5-aminopentyl
            group"

( i x ) FEATURE:
        ( A ) NAME/KEY: Modified-site
        ( B ) LOCATION: 3
        ( D ) OTHER INFORMATION: /note="Tyr at location 3 is
            O- methylated"

( i x ) FEATURE:
        ( A ) NAME/KEY: Modified-site
        ( B ) LOCATION: 11
        ( D ) OTHER INFORMATION: /note="Xaa at location 11 is a
            cyclohexylalanine"

( i x ) FEATURE:
        ( A ) NAME/KEY: Modified-site
        ( B ) LOCATION: 12
        ( D ) OTHER INFORMATION: /note="Glu at location 12 is
            D- configuration"

( x i ) SEQUENCE DESCRIPTION: SEQ ID NO:8:

Gly Asp Tyr Glu Pro Ile Pro Glu Glu Ala Xaa Glu
1               5                   10

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Tyr at location 1 is
            N- substituted with a succinyl group"

( i x ) FEATURE:
        ( A ) NAME/KEY: Modified-site
        ( B ) LOCATION: 10
        ( D ) OTHER INFORMATION: /note="Glu at location 10 is
            D- configuration"

( x i ) SEQUENCE DESCRIPTION: SEQ ID NO:9:

Tyr Glu Pro Ile Pro Arg Gly Asp Phe Glu
1               5                   10

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Gly at location 1 is
            substituted on the alpha carbon with a
            5- guanadinopentyl group"

( i x ) FEATURE:
        ( A ) NAME/KEY: Modified-site
        ( B ) LOCATION: 11
        ( D ) OTHER INFORMATION: /note="Xaa at location 11 is a
            cyclohexylalanine"

( i x ) FEATURE:
        ( A ) NAME/KEY: Modified-site
        ( B ) LOCATION: 12
        ( D ) OTHER INFORMATION: /note="Glu at location 12 is
            D- configuration"

( x i ) SEQUENCE DESCRIPTION: SEQ ID NO:10:

Gly Asp Tyr Glu Pro Ile Pro Glu Glu Ala Xaa Glu
1               5                   10

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Asp at location 1 is N- substituted with a 4-aminomethylbenzoyl group"

( i x ) FEATURE:
  ( A ) NAME/KEY: Modified-site
  ( B ) LOCATION: 10
  ( D ) OTHER INFORMATION: /note="Xaa at location 10 is a
    cyclohexylalanine"

( i x ) FEATURE:
  ( A ) NAME/KEY: Modified-site
  ( B ) LOCATION: 11
  ( D ) OTHER INFORMATION: /note="Glu at location 11 is
    D- configuration"

( x i ) SEQUENCE DESCRIPTION: SEQ ID NO:11:

Asp Trp Glu Pro Ile Pro Glu Glu Ala Xaa Glu
1               5                   10

( 2 ) INFORMATION FOR SEQ ID NO:12:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="Asp at location 1 is
    N- substituted with a 4-guanidinomethylbenzoyl
    group"

( i x ) FEATURE:
  ( A ) NAME/KEY: Modified-site
  ( B ) LOCATION: 10
  ( D ) OTHER INFORMATION: /note="Xaa at location 10 is
    cyclohexylalanine"

( i x ) FEATURE:
  ( A ) NAME/KEY: Modified-site
  ( B ) LOCATION: 11
  ( D ) OTHER INFORMATION: /note="Glu at location 11 is
    D- configuration"

( x i ) SEQUENCE DESCRIPTION: SEQ ID NO:12:

Asp Trp Glu Pro Ile Pro Glu Glu Ala Xaa Glu
1               5                   10

( 2 ) INFORMATION FOR SEQ ID NO:13:

( i ) SEQUENCE CHARACTERISTICS:
  ( A ) LENGTH: 11 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="Asp at location 1 is
    N- substituted with a 4-aminomethyl group"

( i x ) FEATURE:
  ( A ) NAME/KEY: Modified-site
  ( B ) LOCATION: 10
  ( D ) OTHER INFORMATION: /note="Xaa at location 10 is a
    cyclohexylalanine"

( i x ) FEATURE:
  ( A ) NAME/KEY: Modified-site
  ( B ) LOCATION: 11
  ( D ) OTHER INFORMATION: /note="Glu at location 11 is
    D- configuration"

( i x ) FEATURE:
    ( A ) NAME/KEY: Modified-site
    ( B ) LOCATION: 3
    ( D ) OTHER INFORMATION: /note="Tyr at location 3 is
        O- methylated"

( x i ) SEQUENCE DESCRIPTION: SEQ ID NO:13:

Asp Trp Glu Pro Ile Pro Glu Glu Ala Xaa Glu
1               5                   10

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Gly at location 1 is
            N- substituted with a
            4- aminomethylcyclohexylcarbonyl group"

( i x ) FEATURE:
        ( A ) NAME/KEY: Modified-site
        ( B ) LOCATION: 11
        ( D ) OTHER INFORMATION: /note="Xaa at location 11 is a
            cyclohexylalanine"

( i x ) FEATURE:
        ( A ) NAME/KEY: Modified-site
        ( B ) LOCATION: 12
        ( D ) OTHER INFORMATION: /note="Glu at location 12 is
            D- configuration"

( x i ) SEQUENCE DESCRIPTION: SEQ ID NO:14:

Gly Asp Phe Glu Pro Ile Pro Glu Glu Ala Xaa Glu
1               5                   10

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Gly at location 1 is
            N- substituted with a
            4- aminomethylcyclohexylcarbonyl group"

( i x ) FEATURE:
        ( A ) NAME/KEY: Modified-site
        ( B ) LOCATION: 11
        ( D ) OTHER INFORMATION: /note="Xaa at location 11 is a
            cyclohexylalanine"

( i x ) FEATURE:
        ( A ) NAME/KEY: Modified-site
        ( B ) LOCATION: 12
        ( D ) OTHER INFORMATION: /note="Glu at location 12 is
            D- configuration"

( x i ) SEQUENCE DESCRIPTION: SEQ ID NO:15:

Gly Asp Phe Glu Pro Ile Pro Glu Glu Ala Xaa Glu
1               5                   10

(2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Gly at location 1 is
             N- substituted with a
             4- guanidinomethylcyclohexylcarbonyl group"

(ix) FEATURE:
        (A) NAME/KEY: Modified-site
        (B) LOCATION: 11
        (D) OTHER INFORMATION: /note="Xaa at location 11 is a
             cyclohexylalanine"

(ix) FEATURE:
        (A) NAME/KEY: Modified-site
        (B) LOCATION: 12
        (D) OTHER INFORMATION: /note="Glu at location 12 is
             D- configuration"

(xi) SEQUENCE DESCRIPTION: SEQ ID NO:16:

Gly Asp Phe Glu Pro Ile Pro Glu Glu Ala Xaa Glu
   1               5                   10